United States Patent [19]

Casper et al.

[11] Patent Number: 5,167,626
[45] Date of Patent: Dec. 1, 1992

[54] MEDICAL CAPSULE DEVICE ACTUATED BY RADIO-FREQUENCY (RF) SIGNAL

[75] Inventors: Robert A. Casper, Raleigh; Michael L. McCartney, Durham; Warren J. Jochem; Alan F. Parr, both of Cary, all of N.C.

[73] Assignee: Glaxo Inc., Research Triangle Park, N.C.

[21] Appl. No.: 826,407

[22] Filed: Jan. 27, 1992

Related U.S. Application Data

[63] Continuation-in-part of Ser. No. 591,838, Oct. 2, 1990.

[51] Int. Cl.⁵ .............................................. A61M 11/00
[52] U.S. Cl. .................................... 604/93; 604/891.1; 128/769
[58] Field of Search .................... 604/93, 113, 890.1, 604/892.1, 20; 128/769, 631; 600/2, 3, 7

[56] References Cited

U.S. PATENT DOCUMENTS

| | | | |
|---|---|---|---|
| 1,707,762 | 4/1929 | Homan | 604/113 |
| 3,485,235 | 12/1969 | Felson | 128/769 |
| 4,239,040 | 12/1980 | Hosoya et al. | 128/769 |
| 4,439,197 | 3/1984 | Honda et al. | 128/769 |
| 4,481,952 | 11/1984 | Pawelec | 128/769 |
| 4,507,115 | 3/1985 | Kambara et al. | 128/769 |
| 5,122,128 | 6/1992 | Cardinal et al. | 604/890.1 |

*Primary Examiner*—C. Fred Rosenbaum
*Assistant Examiner*—Manuel Mendez
*Attorney, Agent, or Firm*—Richard E. Jenkins

[57] ABSTRACT

A medical capsule device for releasing a substance at a defined location in the gastrointestinal tract. The device has a capsule body defining one or more apertures in the circumferential wall thereof and a sleeve valve rotatably positioned therein having one or more corresponding apertures in the circumferential wall thereof. The sleeve valve comprises a coil and electrically connected heatable resistor which are operatively associated with an actuator member formed of a shape memory alloy responsive to heat and which will move from a non-heated first shape to a heated second shape. Actuator stop means are provided in the capsule body for being engaged by the actuator member during movement from the non-heated first shape to the heated second shape so that the actuator member movement will serve to rotate the sleeve valve to an open position.

10 Claims, 8 Drawing Sheets

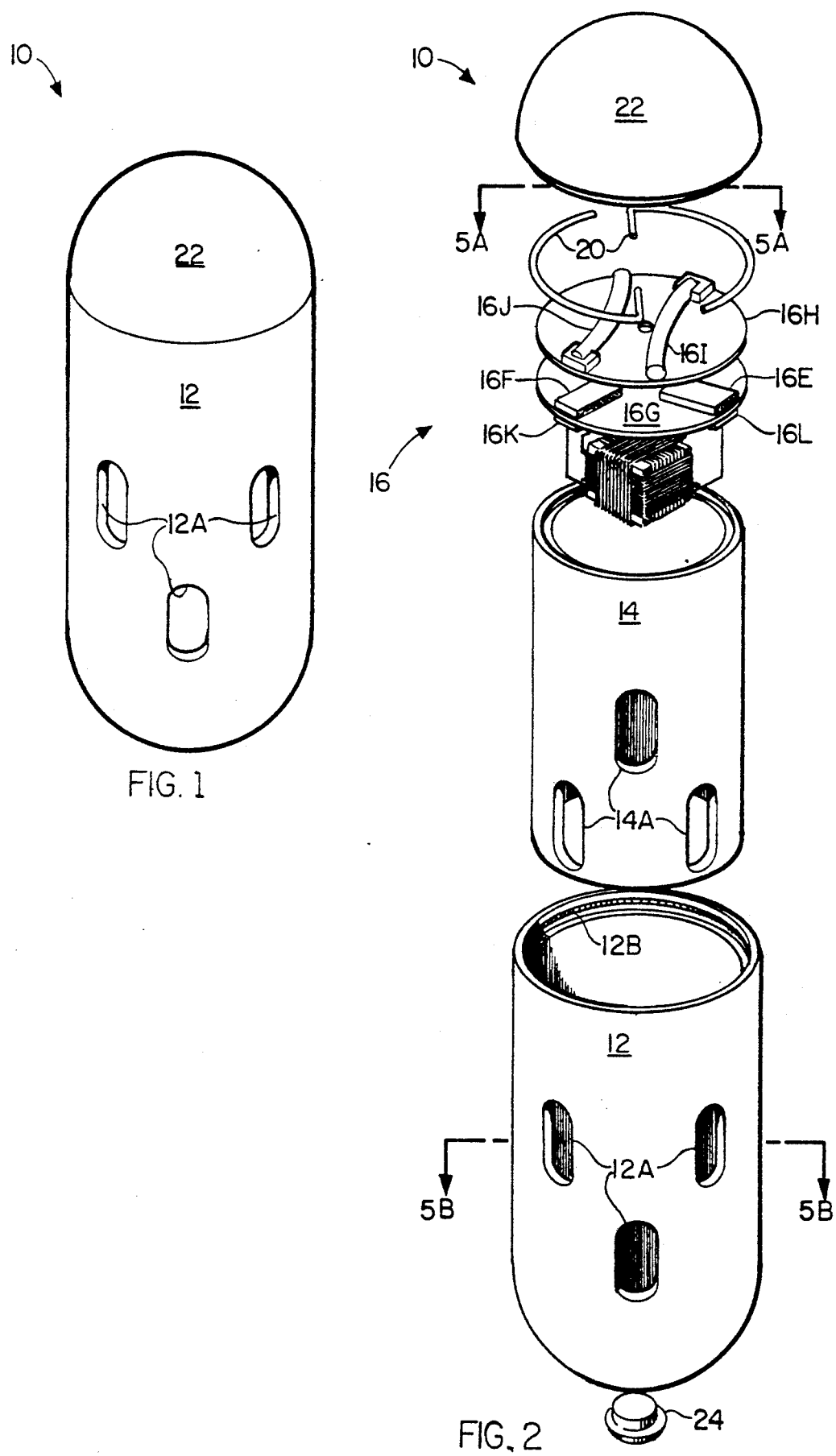

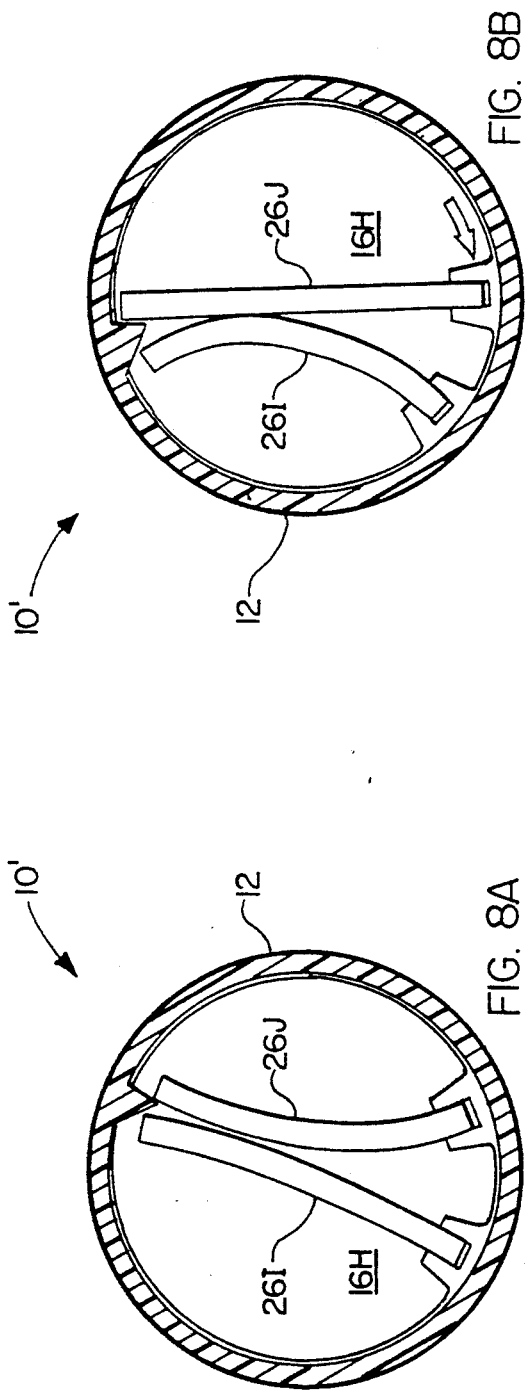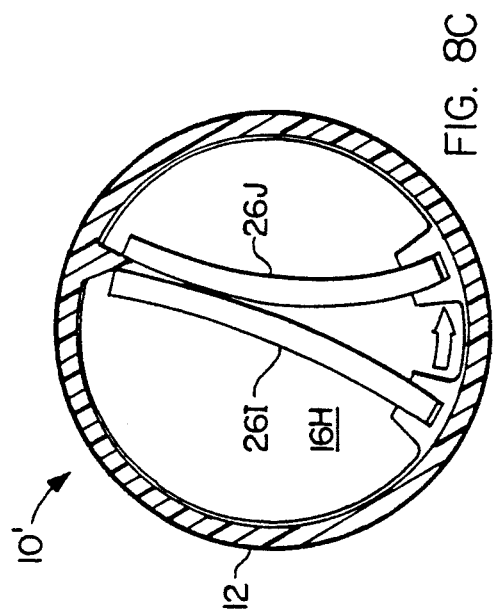

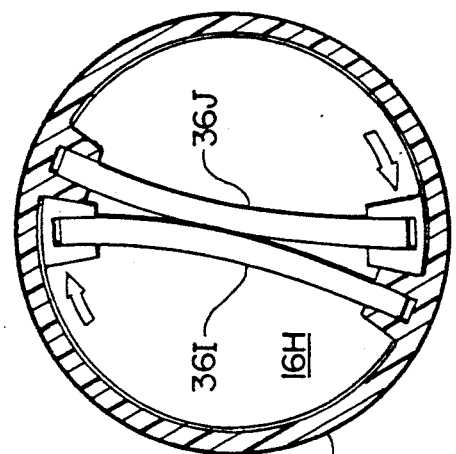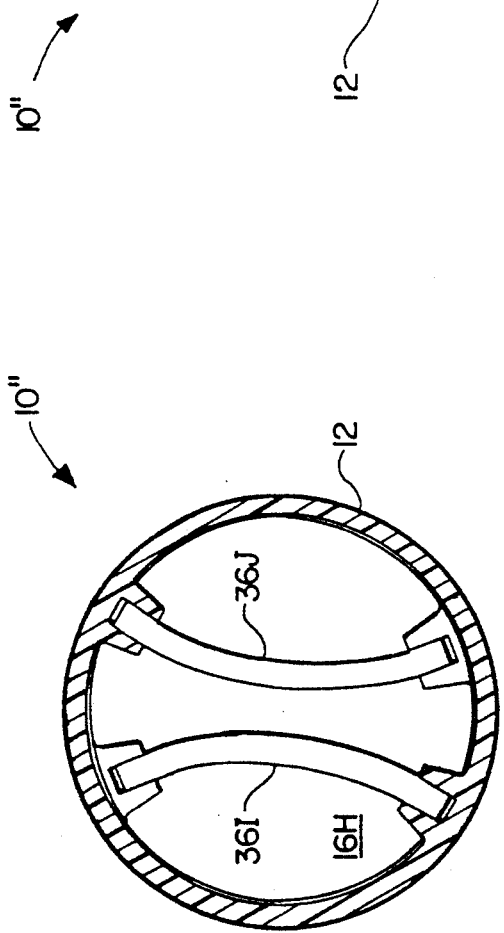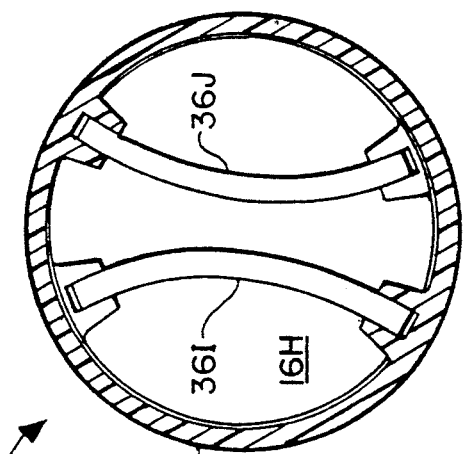

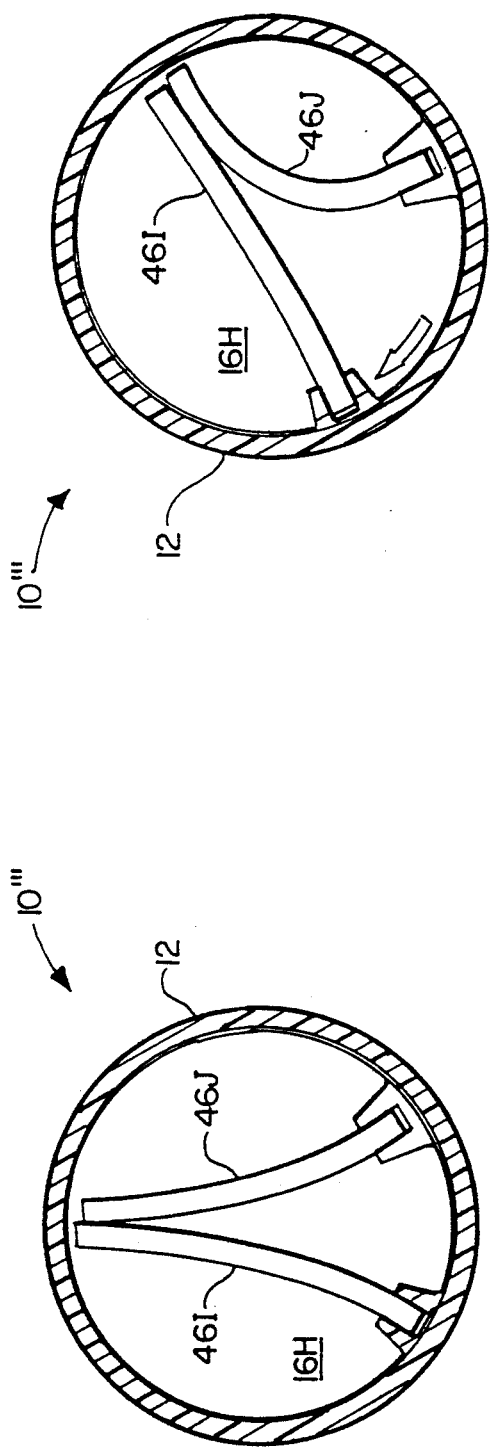
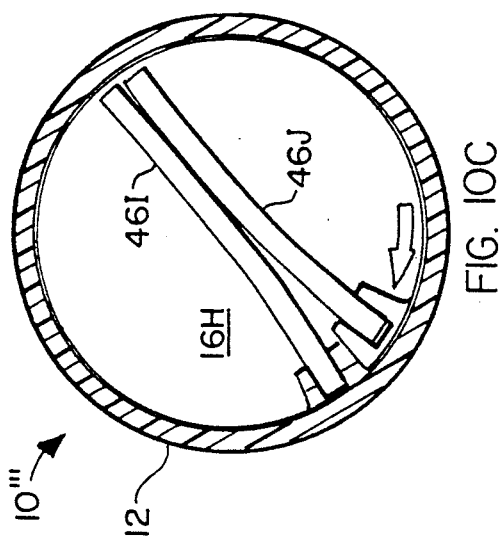

MEDICAL CAPSULE DEVICE ACTUATED BY RADIO-FREQUENCY (RF) SIGNAL

RELATED ART

This application is a continuation-in-part application of Ser. No. 07/591,838 filed Oct. 2, 1990, and now pending.

DESCRIPTION

1. Technical Field

The present invention relates to an improved medical capsule device, and more particularly to an improved medical capsule device adapted for use to release a substance at a defined location in the gastrointestinal tract.

2. Related Art

The delivery of drugs to specific sites within the gastrointestinal tract of humans as well as animals is a challenge in both clinical and research applications. During the research phase of pharmaceutical drug development, nasogastric catheters are often used to deliver a drug to a target site within the gastrointestinal tract as a means of evaluating the absorption thereof. While this is a direct and highly accurate means of establishing the relationship between location and absorption, it does pose some uncertainties. The procedure of insertion of the catheter can result in the release of catecholimines in the subject, and it could introduce responses which would interfere with the absorption or action of the drug. Moreover, the presence of the catheter in the gastrointestinal tract can cause local mechanical disturbances which further distort the responses to the drug.

One conventional solution to the problem of site-specific drug delivery is to place the drug in an untethered ingestible enclosure and to thereafter release the drug by remote control. The location of the drug prior to release can be continuously monitored by radiographic methods such as X-ray or scintigraphy as well as by radio-frequency (RF) goniometry.

Several conventional remote control drug release capsules are well known to those skilled in the art. For example, U.S. Pat. No. 4,425,117 to Hugeman et al. discloses a remote control drug release capsule which is actuated by application of a radio-frequency signal thereto. The radio-frequency energy serves to heat a thin wire within the capsule which in turn burns through a thread so as to release a spring-actuated lance. The lance is driven into a latex sphere contained within the capsule which is filled with a pharmaceutical drug and thereby releases the drug into the environment of the capsule. However, this complex capsule device has been found to be very difficult to load with a drug since the latex sphere must be filled under slight pressure and then sealed.

Another conventional, remote-control medical capsule device is disclosed in U.S. Pat. No. 4,507,115 to Kambara et al. The capsule device comprises a capsule body defining a chamber therein and a through-hole at the top thereof which is dimensioned so that it prevents medical fluid contained in the chamber from easily leaking. A slidably movable piston is positioned within the body member so as to move axially in the chamber from a liquid-receiving position to a liquid-pushing position. The piston is actuated by a shape memory alloy helical spring which will force the piston to the liquid-pushing position when heated by ultrasonic waves applied from a remote ultrasonic heating means. This capsule has certain shortcomings in view of the ultrasonic actuation as well as the drug release from only a single aperture which could possibly render specific site application more difficult in the gastrointestinal tract. Also, the high concentration of drug at the singular release site could potentially be damaging to the intestinal mucosa.

The present invention is therefore intended to eliminate the shortcomings of these and other remote control drug delivery capsules and to provide a remote control drug delivery capsule device which is safe and reliable in use and possesses capabilities not heretofore known.

DISCLOSURE OF THE INVENTION

The medical capsule device according to the invention comprises a capsule body having one or more apertures in the circumferential wall thereof. A rotatably movable sleeve member is positioned within the capsule body which has one or more apertures in the circumferential wall thereof corresponding to the apertures in the capsule body, and the sleeve member is rotatably movable from a closed position at which the apertures thereof are not in circumferential registration with the capsule body apertures to an open position at which the apertures thereof are in circumferential registration with the capsule body apertures.

An actuator means is positioned in the sleeve member for providing rotatable movement to the sleeve member from the closed position to the open position wherein a drug may be released from the capsule or an external substance collected by the capsule. The actuator means comprises (1) a circuit tuned to a magnetic field of high frequency comprising a coil and capacitor electrically connected to a heatable resistance member and (2) an actuator member which is operatively associated with the circuit and made of a shape memory alloy responsive to heat applied thereto by the resistance member so as to move from a non-heated first shape to a heated second shape. An actuator stop means associated with the capsule body is provided for being engaged by the actuator member during movement from its non-heated first shape to its heated second shape so that the actuator member movement will thereby serve to rotatably move the sleeve member relative to the capsule body from the closed position to the open position.

It is therefore the object of this invention to provide a remote control medical capsule device which will safely and reliably release a substance at a predetermined location in the gastrointestinal tract of a human or animal.

It is another object of the present invention to provide a remote control medical capsule device which will safely and precisely deliver drugs (e.g., anti-ulcer and chemotherapeutic drugs) to specific predetermined sites in the gastrointestinal tract.

It is yet another object of the present invention to provide a remote control medical capsule device which is adapted to be easily actuated and to provide a large aperture area upon actuation thereof.

It is yet another object of the present invention to provide a remote control medical capsule device which is adapted to receive and be actuated by a radio-frequency signal regardless of the orientation of the device within the gastrointestinal tract.

It is still another object of the present invention to provide a remote control medical capsule device which is adapted to both open and close upon actuation thereof at a predetermined location in the gastrointestinal tract.

Some of the objects of the invention having been stated, other objects will become evident as the description proceeds, when taken in connection with the accompanying drawings.

BRIEF DESCRIPTION OF THE DRAWINGS

FIG. 1 is a perspective view of a medical capsule device according to the present invention;

FIG. 2 is an exploded view of the capsule device;

FIGS. 8A-8C are views taken similarly to FIGS. 5A and 6A and show a second embodiment of the capsule device in its sequence of closed, open and closed positions, respectively;

FIGS. 9A-9C are views taken similarly to FIGS. 5A and 6A showing a third embodiment of the capsule device in its sequence of closed, open and closed positions, respectively; and FIGS. 10A-10C are views taken similarly to FIGS. 5A and 6A showing a fourth embodiment of the capsule device in its sequence of closed, open and closed positions, respectively.

BEST MODE FOR CARRYING OUT THE INVENTION

Figure 3:
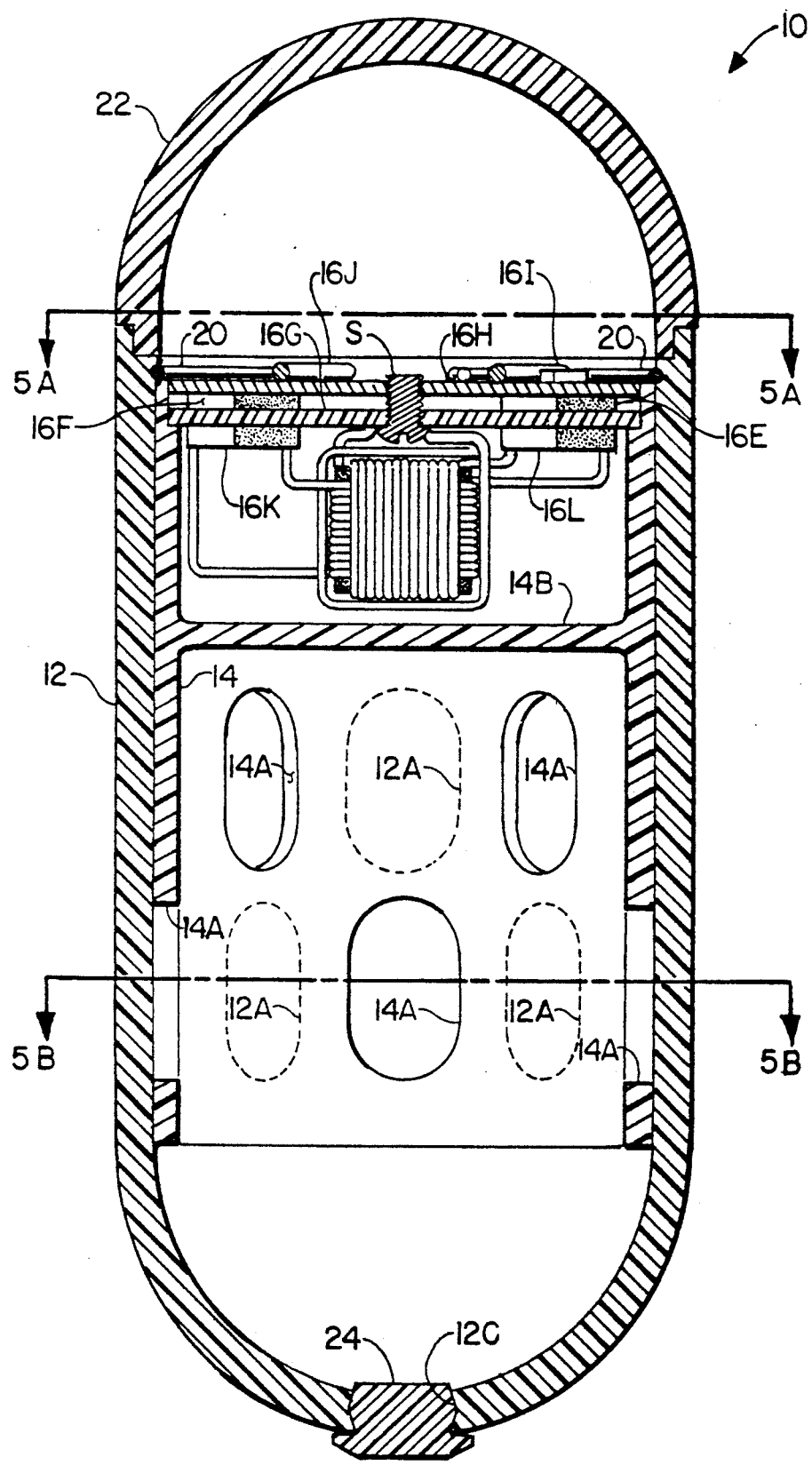
FIG. 3 is a vertical cross-sectional view of the capsule device.

Referring now more specifically to the drawings, FIGS. 1-3 show an embodiment of the present invention which is generally designated 10.

Capsule device 10 includes a capsule body 12 and a sleeve member 14 which is slidably received and rotatably mounted within capsule body 12. Capsule body 12 and sleeve member 14 each include a plurality of apertures, 12A and 14A, respectively, which are in circumferential registration when capsule device 10 is actuated and sleeve member 14 rotates therein to the capsule's open position. An actuator mechanism 16 resides in the top portion of sleeve member 14 and is separated from the bottom portion of sleeve member 14 by a fluid impermeable wall or partition 14B. A pair of retainer wires 20 are fixedly positioned within retainer wire groove 12B defined around the inner surface of the top of capsule body 12. Retainer wires 20 serve as a fulcrum when actuator mechanism 16 is energized by heat derived from a magnetic field and thereby imparts rotatable movement to sleeve member 14 to which it is secured. A cap 22 is provided to seal the top of the capsule when sleeve member 14 is positioned therein, and a fill plug 24 is provided in an aperture 12C in the bottom of capsule body 12 in order to facilitate introduction of a selected material. It is presently contemplated that capsule body 12, sleeve member 14, cap 22 and fill plug 24 may be formed from a PTFE compound (e.g., TEFLON) or acetal resin (e.g., DELRIN) although any other radio-frequency transparent materials could suitably be used.

Figure 4:
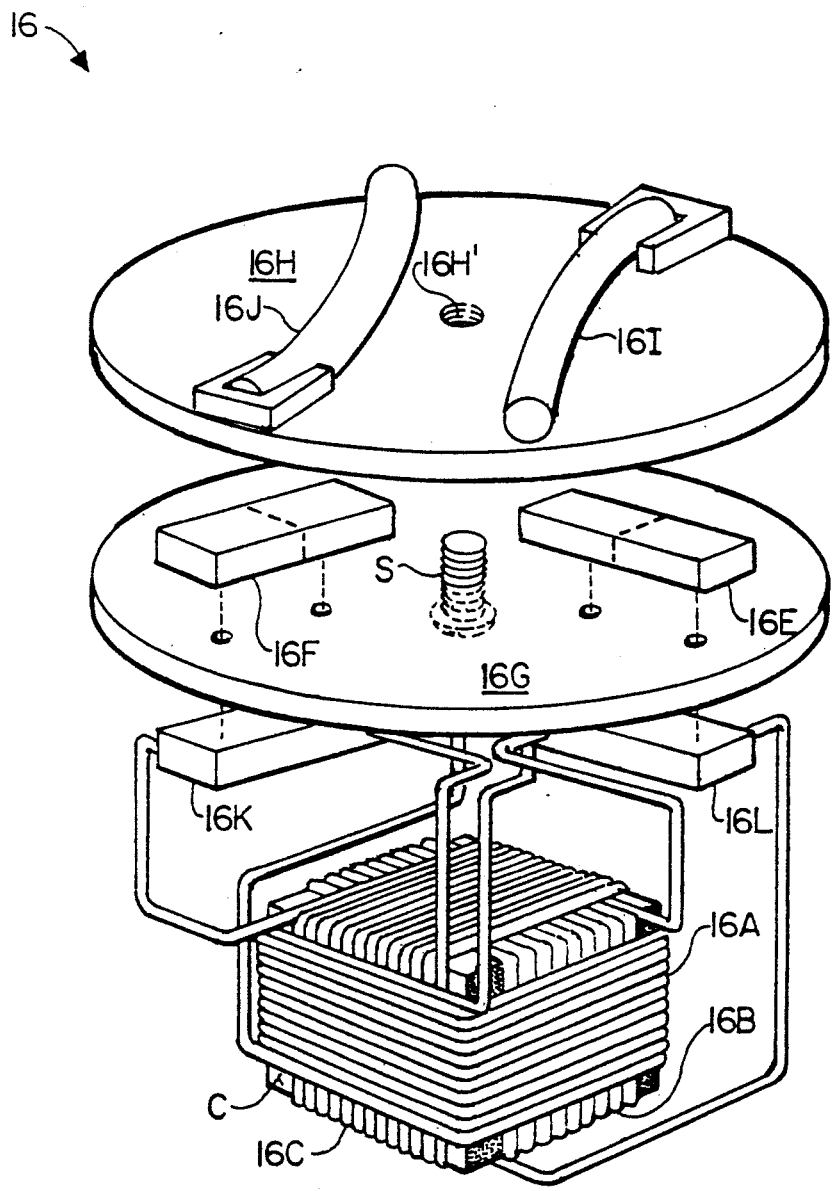
FIG. 4 is an enlarged view of the actuator mechanism for opening the apertures in the capsule device.
Figure 6B:
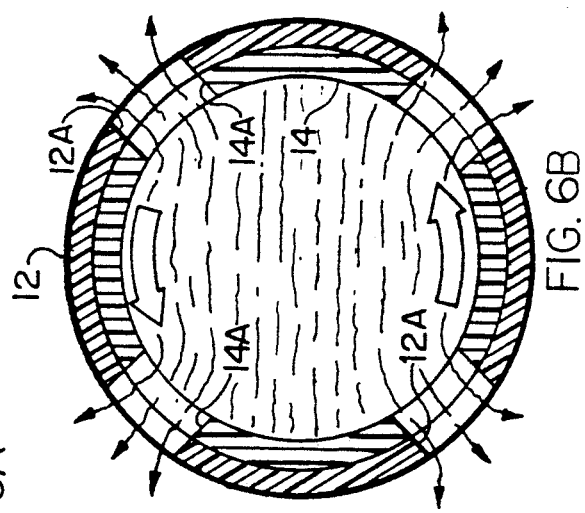
FIGS. 6A and 6B are taken on the lines 6A—6A and 6B—6B, respectively, of FIGS. 2 and 3 and show the capsule device in its open position subsequent to actuation by application of a magnetic field.
Figure 6A:
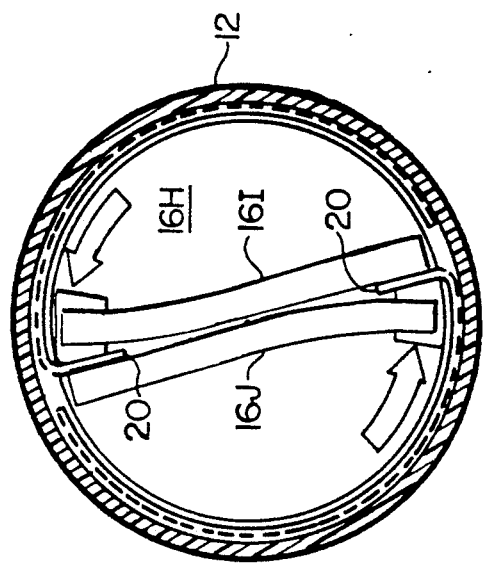
Figure 5B:
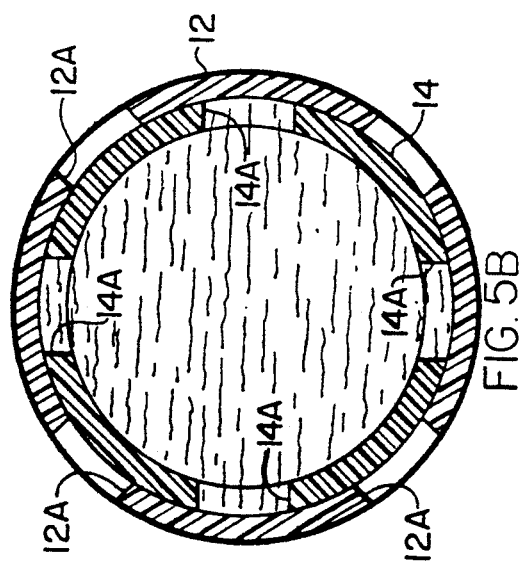
FIGS. 5A and 5B are taken on the lines 5A—5A and 5B—5B, respectively, of FIGS. 2 and 3 and show the capsule device in its closed position prior to actuation by application of a magnetic field.
Figure 5A:
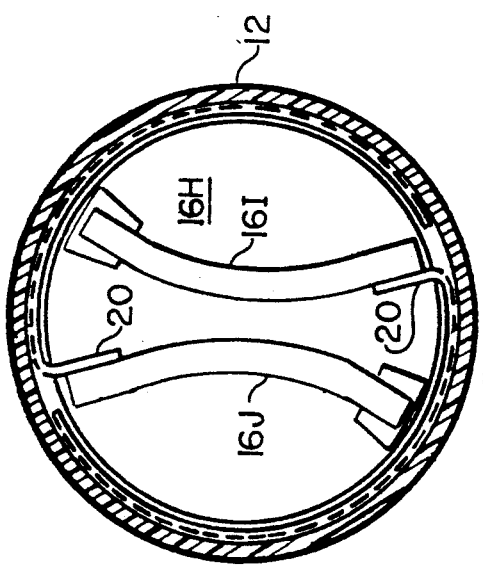
Figure 7:
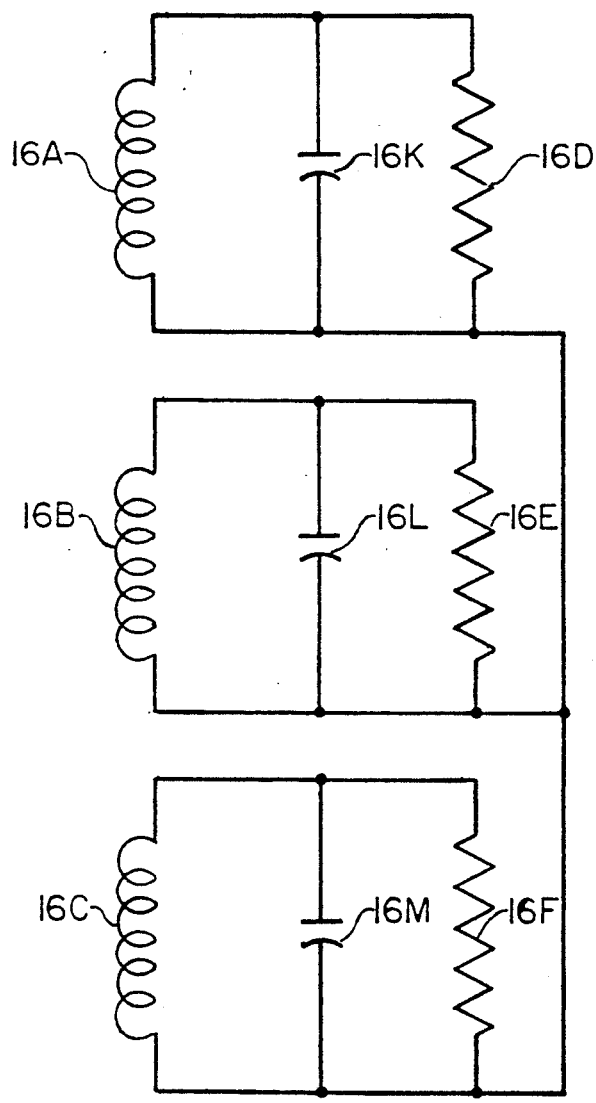
FIG. 7 is a schematic diagram of the circuit of the capsule device for receiving radio-frequency (RF) signals when a magnetic field is applied thereto.

With specific reference now to FIGS. 4 and 7, actuator mechanism 16 will be described in more detail for a more complete appreciation of the instant invention. Three copper wire coils 16A-16C (see FIG. 4) are orthogonally wound around a common ferrite core C. Ferrite core C serves to increase the effective cross-sectional area of coils 16A-16C and to thereby provide for the interception of more flux from the magnetic field transmitter (not shown) and minimize the dependence of received radio-frequency signal energy on the orientation of capsule device 10 within the gastrointestinal tract. Most suitably, coils 16A-16C are tuned to the transmitter frequency with capacitors and to apply the received radio-frequency signal directly to resistive heaters 16D-16F (for example, Bourns CR1206 brand 1000 ohm resistors) without the necessity of rectification and filtering of the signal. Resistive heaters 16D-16F are mounted on circuit board 16G which is in turn secured to metallic heat plate 16H by a screw S passing through circuit board 16G and into a tapped hole 16H' in metallic heat plate 16H. Resistive heaters 16D-16F are each electrically connected to a respective one of coils 16A-16C and to corresponding capacitors 16K-16M mounted beneath circuit board 16G so that any magnetic flux received by one or more of respective coils 16A-16C will induce an RF current which will be converted to heat by resistive heaters 16D-16F and applied to heat plate 16H.

Thermally conductive grease (not shown) is used to improve thermal energy transfer between resistive heaters 16D-16F and metallic heat plate 16H. Two shape memory metal fingers 16I, 16J are each secured at one respective end thereof to heat plate 16H, and each extends across and parallel with heat plate 16H. Thermally conductive grease is also used to insure good thermal contact between metal fingers 16I, 16J and heat plate 16H. Although many materials would be suitable for forming fingers 16I, 16J, nickel titanium was used for the instant invention.

It is desirable to form fingers 16I, 16J from shape memory alloys since the material can be made to have a transition temperature in the range of normal mammalian body temperatures. This is advantageous since the shape or configuration transition occurs relatively abruptly with temperature, and it is generally necessary to elevate the temperature of fingers 16I, 16J only a few degrees to effect rotatable movement of sleeve member 14 within capsule body 12. This is desirable for an ingestible device such as capsule device 10 since it is not necessary to raise the temperature of any part of device 10 significantly above that of the body temperature to cause actuation thereof, and thus the total energy delivered can be limited to a safe, nominal amount.

As can now be appreciated, actuator mechanism 16 and sleeve member 14 essentially serve as a sleeve valve to release a drug or other substance from the reservoir space in capsule device 10 defined generally between the lower compartment of sleeve member 14 and capsule body 12. Shape memory alloy fingers 16I, 16J will tend to straighten when acted on by heat from resistive heaters 16D-16F and by applying force against retainer wires 20 (see FIGS. 5A-5B and 6A-6B) will thus serve to rotate sleeve member 14 within capsule body 12. This movement opens the capsule by positioning apertures 14A of sleeve member 14 and apertures 12A of capsule body 12 in circumferential registration. The sleeve valve takes advantage of the relatively large aperture area which may be achieved with only a small rotational relative displacement of sleeve member 14 within capsule body 12. Though the instant invention may be made with only a single through-put aperture in capsule device 10, preferably a plurality of apertures are provided around the circumference of sleeve member 14 and capsule body 12 to (1) assure that the release time of a drug carried thereby is not dependent on the orientation of the capsule device in the gastrointestinal tract and (2) to decrease the possible negative effects of high drug concentration on the gastrointestinal mucosa.

Although other means are possible, location of capsule device 10 may most suitably be determined by scintigraphy. By introducing a small amount of radioactive material into the drug or other material carried by capsule device 10, the device may be followed in the gastrointestinal tract with a conventional scintigraphic imaging system. Radioactive material could also be placed on capsule device 10 in order to follow the capsule as well as the drug released thereby. Other methodology to determine the movement and location of capsule device 10 in the gastrointestinal tract would include X-ray, radar and sonar techniques which would be familiar to those skilled in the art.

While not shown in the drawings and not a per se element of the instant invention, it is contemplated that the external transmitter for creating a high-frequency magnetic field to actuate capsule device 10 will be an electrostatically shielded coil which is energized by a radio-frequency power amplifier. Electrostatic shielding should be used to remove the large electrical field generated in the vicinity of the coil and thereby prevent electrical shock hazards and dielectric heating of tissues associated with the fields. The shielding results in a radio-frequency field which has only a magnetic component. Most suitably, the external transmitter will be positioned in proximity to the body of a person or animal having ingested capsule device 10 and will generate a radio-frequency magnetic field at 6.78 MHz (a frequency set aside for industrial heating applications) which coils 16A-16C and capacitors 16K-16M have been tuned to receive.

APPLICATIONS FOR THE CAPSULE DEVICE

Capsule device 10 may be used to evaluate the absorption of a drug from various sites of the gastrointestinal tract under non-invasive conditions. The information contained about regional drug absorption via the capsule device will aid in future development of complex site-specific drug dosage forms. Yet another application of capsule device 10 would be to deliver highly toxic drugs to specific sites in the gastrointestinal tract in a clinical setting. For example, the capsule device could be used to deliver chemotherapeutic drugs to the colon of patients who have colon cancer as well as to deliver drugs that are effective at treating ulcerative colitis of the colon but which are irritating to the small intestine. In this application, capsule device 10 would be administered and function in the same manner as under the first application.

ALTERNATIVE EMBODIMENTS OF THE CAPSULE DEVICE ADAPTED TO BOTH OPEN AND CLOSE

Applicants also contemplate alternative embodiments of the instant invention wherein the capsule device is adapted to both open and close upon actuation thereof in order to release and/or collect a substance at a predetermined location in the gastrointestinal tract of a human or animal. The alternative embodiments of the capsule device provide for other uses of the capsule device such as to sample the liquid environment of the gastrointestinal tract. This would permit the monitoring of drugs, enzymes, and bacteria as well as other intestinal compounds under non-invasive conditions. For this application, one of the alternative embodiments of the capsule device could be administered orally (as with the first embodiment of the invention described hereinbefore) but the capsule would be empty and the aperture closed when administered. At the desired location in the gastrointestinal tract, the capsule would be actuated so as to open to collect the desired gastrointestinal tract samples and the capsule would then be closed so as to trap the samples therein for examination subsequent to elimination from the body.

The aforementioned example is only representative of the many potential uses of the alternative embodiments of the subject invention wherein the capsule device is adapted to open and then close upon actuation. Other applications would be well known and appreciated by one skilled in this art.

While the alternative embodiments of the capsule device could be constructed in a variety of configurations, applicants hereinbelow wish to describe three representative embodiments of the capsule device which are adapted to both open and close upon actuation. The three alternative embodiments of the capsule device each have the capability of going from closed, to open, to closed under the influence of the same type of actuation as the original embodiment of capsule device 10 described in detail hereinbefore.

The first alternative embodiment of the capsule device, generally designated 10', is shown in FIGS. 8A-8C wherein shape memory alloy fingers 16I, 16J of capsule device 10 have been replaced with leaf spring 26I and shape memory alloy finger 26J. Leaf spring 26I and shape memory alloy finger 26J are each secured at one respective end thereof to heat plate 16H, and each extends across and parallel with heat plate 16H as shown in FIGS. 8A-8C. When capsule device 10' is swallowed and at body temperature, shape memory alloy finger 26J is below its Austenitic and Martensitic temperatures so that capsule device 10' is closed and leaf spring 26I maintains the capsule in the closed position (see FIG. 8A). When capsule device 10' reaches the desired sampling site, power is applied by means of the previously described radio frequency signal and shape memory alloy finger 26J is heated above its Martensitic temperature which causes finger 26J to straighten and thereby to open capsule device 10' (see FIG. 8B). Opening of capsule device 10' serves to compress leaf spring 26I as also best seen in FIG. 8B.

When the radio frequency signal is discontinued, shape memory alloy finger 26J cools to body temperature which is below its Austenitic transition temperature and finger 26J becomes sufficiently soft that leaf spring 26I acts to redeform it and thereby to close capsule device 10' (see FIG. 8C). As a matter of design choice, shape memory alloy finger 26J must be selected with Austenitic and Martensitic transition temperatures sufficiently close that high temperatures are not required for operation of capsule device 10', and leaf spring 26I must be configured so as to be powerful enough to rebend finger 26J without offering excessive resistance to finger 26J during opening of capsule device 10'.

With reference now to FIGS. 9A-9C, a second embodiment of the alternative open-and-close embodiments of capsule device 10 is illustrated which is generally designated 10". Capsule device 10" incorporates two-way shape memory alloy fingers 36I, 36J. Alloy fingers 36I, 36J are each secured at one respective end thereof to heat plate 16H and at the other respective end thereof to capsule body 12 as shown in FIGS. 9A-9C. Fingers 36I, 36J will serve to alternate between two shapes as they are cycled above their Martensitic transition temperature and below their Austenitic transition temperature rather than simply becoming soft. Thus, closed capsule device 10" (see FIG. 9A) will be opened by fingers 36I, 36J upon heating thereof above the Martensitic temperature (see FIG. 9B), and fingers 36I, 36J will serve to close capsule device 10" upon a return to body temperature (see FIG. 9C) which is below the Austenitic temperature of the shape memory alloy fingers. Although the selection of appropriate shape memory alloy materials from which to form fingers 36I, 36J is a matter of design choice, it is known that two-way materials which can develop significant forces during both shape transformations are represented by alloys such as copper/zinc/aluminum (CZA).

Referring now to FIGS. 10A-10C, a third alternative embodiment of the open-and-close alternative embodiments of capsule device 10 is shown therein which is generally designated 10'''. Capsule device 10''' comprises a pair of one-way shape memory alloy fingers, 46I, 46J, which have different Martensitic transition temperatures, and preferably, both fingers 46I, 46J have Austenitic transition temperatures near body temperature. One end of finger 46I is secured to capsule body 12 and one end of finger 46J is secured to heat plate 16H, and the other ends of alloy fingers 46I, 46J are in contact with one another as shown in FIGS. 10A-10C. In use, upon initial heating of closed capsule device 10''' (see FIG. 10A), the actuator with the lowest Martensitic temperature, 46I, recovers its shape and serves to open capsule device 10''' (see FIG. 10B). A second heating serves to further elevate the temperature of both fingers 46I, 46J and thereby raises finger shape memory alloy finger 46J to its Martensitic transition temperature so as to cause shape recovery and continued rotation of capsule body 12 in the same direction relative to sleeve member 14 until capsule device 10''' is again closed (see FIG. 10C). In this alternative embodiment of the invention, the stiffness of finger 46I remains high since it is above its Martensitic transition temperature and it can be used as a fulcrum by finger 46J during shape recovery thereof.

It will be understood that various details of the invention may be changed without departing from the scope of the invention. Furthermore, the foregoing description is for the purpose of illustration only, and not for the purpose of limitation—the invention being defined by the claims.

What is claimed is:

1. A medical capsule device adapted for release and/or collection of a substance at a defined location in the alimentary tract, said device comprising:
    a capsule body defining one or more apertures in the circumferential wall thereof;
    a rotatably movable sleeve member positioned within said capsule body and defining one or more apertures in the circumferential wall thereof corresponding to said apertures in said capsule body, said sleeve member adapted to be rotatably movable from a closed position at which said apertures thereof are not in registration with said capsule body apertures to an open position at which said apertures thereof are in registration with said capsule body apertures and back to said closed position;
    actuator means positioned in said sleeve member for rotatably moving said sleeve member and comprising (1) a circuit inductively coupled to an alternating magnetic field and operatively connected with (2) at least one actuator member made of a shape memory alloy responsive to heat obtained from said circuit; and
    actuator engagement means associated with said capsule body and engaged by said actuator member during heat responsive movement so that said actuator member movement will thereby serve to rotatably move said sleeve member from said closed position to said open position and back to said closed position.

2. A medical capsule device according to claim 1 wherein said capsule body defines a plurality of spaced-apart apertures around the circumference thereof.

3. A medical capsule device according to claim 1 wherein said capsule body includes a removable plug at one end thereof to facilitate the insertion of a substance therein or the removal of a substance therefrom.

4. A medical capsule device according to claim 3 wherein said capsule body further includes a removable cap at the other end thereof to facilitate insertion and removal of said sleeve member therefrom.

5. A medical capsule device according to claim 1 wherein said sleeve member defines a first open compartment at one end for receiving said actuator means and a second open compartment at the other end for receiving a substance to be released and/or collected, said compartments being separated by a fluid impermeable wall therebetween and said one or more apertures being located in the circumferential wall of said second compartment.

6. A medical capsule device according to claim 5 wherein said one or more apertures in said sleeve member comprises a plurality of spaced-apart apertures around the circumference of said second open compartment thereof.

7. A medical capsule device according to claim 1 wherein said circuit comprises a ferrite core having three coils orthogonally wound thereon wherein each coil is electrically connected to a respective capacitor and a respective heatable resistor, and wherein a heat conductive plate is secured to said sleeve member and operatively connected to said heatable resistors.

8. A medical capsule device according to claim 7 wherein said actuator means comprises a shape memory alloy finger and an elongate finger-like spring each secured at one end to said heat conductive plate so the secured ends thereof are spaced apart and both, said shape memory alloy finger and said finger-like spring extend generally in the same direction, said shape memory alloy finger being adapted to engage said actuator engagement means with the other end thereof and to compress said finger-like spring against said actuator engagement means when imparting opening rotational movement to said sleeve member, and said finger-like spring being adapted to engage said actuator engagement means when imparting closing rotational movement to said sleeve member.

9. A medical capsule device according to claim 7 wherein said actuator means comprises a pair of two-way shape memory alloy fingers which are each secured at one end to said heat conductive plate and which engage said actuator engagement means with the other end thereof, said fingers being adapted to impart opening rotational movement to said sleeve member when heated and to impart closing rotational movement to said sleeve member when not heated.

10. A medical capsule device according to claim 7 wherein said actuator means comprises a pair of shape memory alloy fingers having different Martensitic transition temperatures wherein the first of said fingers is secured at one end to said heat conductive plate and the second of said fingers is secured at one end to said capsule body, said shape memory alloy fingers being adapted for engagement at the unsecured ends thereof so as to impart opening rotational movement to said sleeve member when heated to said first Martensitic transition temperature, and to impart second and closing rotational movement in the same direction to said sleeve member when heated to said second Martensitic transition temperature.

* * * * *